United States Patent [19]
Lang et al.

[11] Patent Number: 5,880,156
[45] Date of Patent: Mar. 9, 1999

[54] SUBSTITUTED BENZOYLGUANIDINES, PROCESS FOR THEIR PREPARATION, THEIR USE AS A MEDICAMENT OR DIAGNOSTIC AND MEDICAMENT CONTAINING THEM

[75] Inventors: Hans-Jochen Lang, Hofheim; Heinz-Werner Kleemann, Bad Homburg; Wolfgang Scholz, Eschborn; Udo Albus, Florstadt, all of Germany

[73] Assignee: Hoechst Aktiengesellschaft, Frankfurt am Main, Germany

[21] Appl. No.: 898,889

[22] Filed: Jan. 30, 1996

Related U.S. Application Data

[63] Continuation of Ser. No. 449,260, May 24, 1995, abandoned, which is a continuation of Ser. No. 253,273, Jun. 2, 1994, abandoned.

[30] Foreign Application Priority Data

Jun. 4, 1993 [DE] Germany .......................... 43 18 658.0

[51] Int. Cl.⁶ ...................... A61K 31/165; C07C 321/24; C07C 233/77
[52] U.S. Cl. ........................ 514/618; 514/520; 514/521; 514/523; 514/524; 514/619; 514/620; 558/411; 558/415; 564/162; 564/163; 564/164; 564/165; 564/170; 564/171; 564/142
[58] Field of Search ...................................... 514/520, 521, 514/523, 524, 618, 619, 620; 564/162, 163, 164, 165, 170, 171, 142; 558/411, 415

[56] References Cited

U.S. PATENT DOCUMENTS

| 3,780,027 | 12/1973 | Cragoe et al. | 549/494 |
| 5,091,394 | 2/1992 | Englert et al. | 514/331 |
| 5,292,755 | 3/1994 | Englert et al. | 514/331 |

FOREIGN PATENT DOCUMENTS

| A-0416499 | 3/1991 | European Pat. Off. |
| A-0556672 | 8/1993 | European Pat. Off. |
| A-0556674 | 8/1993 | European Pat. Off. |
| A-3502629 | 7/1986 | Germany . |

*Primary Examiner*—Shailendra Kumar
*Attorney, Agent, or Firm*—Finnegan, Henderson, Farabow, Garrett & Dunner, L.L.P.

[57] ABSTRACT

Substituted benzoylguanidines, process for their preparation, their use as a pharmaceutical or diagnostic, and pharmaceutical containing them Benzoylguanidines of the formula I

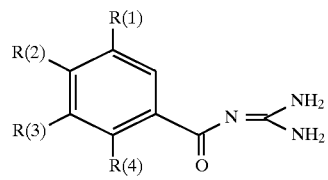

are described in which:

R(1), R(2), R(3), R(4) are as defined in the specification, and pharmaceutically tolerated salts thereof.

6 Claims, No Drawings

SUBSTITUTED BENZOYLGUANIDINES, PROCESS FOR THEIR PREPARATION, THEIR USE AS A MEDICAMENT OR DIAGNOSTIC AND MEDICAMENT CONTAINING THEM

This application is a continuation of prior application Ser. No. 08/449,260 filed May 24, 1995 now abandoned; which is a continuation of application Ser. No. 08/253,273 filed Jun. 2, 1994, now abandoned.

The invention relates to benzoylguanidines of the formula I

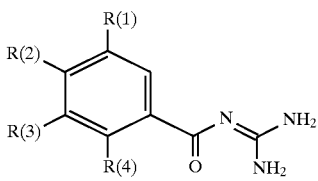

in which:
R(1) is hydrogen, F, Cl, Br, I, —$NO_2$, —C≡N, $X_o$—($CH_2$)$_p$—($CF_2$)$_q$—$CF_3$, R(5)—$SO_m$, R(6)—CO— or R(6)R(7)N—$SO_2$—, where
X is oxygen, S or NR(14),
m is zero, 1 or 2,
o is zero or 1,
p is zero, 1 or 2,
q is zero, 1, 2, 3, 4, 5 or 6,
R(5) and R(6) are ($C_1$–$C_8$)-alkyl, ($C_3$–$C_6$)-alkenyl, —$C_nH_{2n}$—R(8) or $CF_3$,
n is zero, 1, 2, 3 or 4,
R(8) is ($C_3$–$C_7$)-cycloalkyl or phenyl which is unsubstituted or substituted by 1–3 substituents from the group comprising
F, Cl, $CF_3$, methyl, methoxy and NR(9)R(10) where R(9) and R(10) are H or $C_1$–$C_4$-alkyl,
where R(6) also has the meaning of H,
R(7) is H or ($C_1$–$C_4$)-alkyl,
where R(6) and R(7) together can be 4 or 5 methylene groups, of which one $CH_2$ group can be replaced by oxygen, S, NH, N—$CH_3$ or N-benzyl, R(2) is

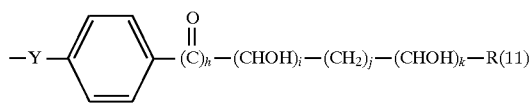

or

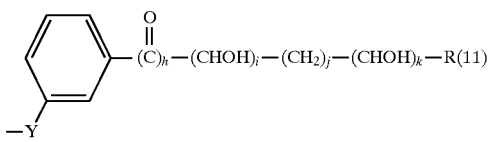

or

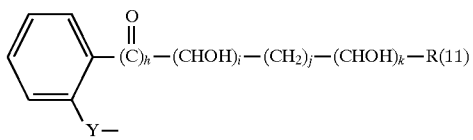

where Y is oxygen, —S— or —NR(12)—,
R(11) and R(12)=hydrogen or ($C_1$–$C_3$)-alkyl, and
h is zero or 1, and
i, j and k independently are zero, 1, 2, 3 or 4, but where h, i and k are not simultaneously zero, R(3) is defined as R(1), or is ($C_1$–$C_6$)-alkyl or —X—R(13) where
X is oxygen, S, NR(14),
R(14) is H or ($C_1$–$C_3$)-alkyl,
R(13) is H, ($C_1$–$C_6$)-alkyl, ($C_3$–$C_8$)-cycloalkyl or —$CbH_{2b}$—R(15) where
b is zero, 1, 2, 3 or 4 and where R(13) and R(14) together can also be 4 or 5 methylene groups and a $CH_2$ group can be replaced by oxygen, S, NH, N—$CH_3$ or N-benzyl,
R(15) is phenyl which is unsubstituted or substituted by 1–3 substituents from the group comprising F, Cl, $CF_3$, methyl, methoxy and NR(9)R(10) where R(9) and R(10) are H or ($C_1$–$C_4$)-alkyl,
R(4) is hydrogen, —OR(16) or —NR(16)R(17) where R(16) and R(17) are independently hydrogen or ($C_1$–$C_3$) -alkyl
and their pharmaceutically tolerable salts.

Preferred compounds of the formula I are those in which:
R(1) is hydrogen, F, Cl, —C≡N, —$CF_3$, R(5)—$SO_m$, R(6)—CO— or R(6)R(7)N—$SO_2$—, where
m is zero, 1 or 2,
R(5) and R(6) are ($C_1$–$C_8$)-alkyl, ($C_3$–$C_4$)-alkenyl, —$C_nH_{2n}$—R(8) or —$CF_3$,
n is zero or 1,
R(8) is ($C_3$–$C_6$)-cycloalkyl or phenyl, which is unsubstituted or substituted by 1–3 substituents from the group comprising F, Cl, $CF_3$, methyl, methoxy and NR(9)R(10) where R(9) and R(10) are H or methyl,
where R(6) also has the meaning of H,
R(7) is H or methyl,
R(3) is hydrogen, methyl, cyano, —$CF_3$, F or Cl and the other radicals are as defined above, and their pharmaceutically tolerable salts.

Particularly preferred compounds I are those in which:
R(1) is hydrogen, F, Cl, —C≡N, —$CF_3$, R(5)—$SO_m$, R(6)—CO— or R(6)R(7)N—$SO_2$—, where
m is zero, 1 or 2,
R(5) is methyl or $CF_3$,
R(6) and R(7) independently of one another are H or methyl;
R(2) is

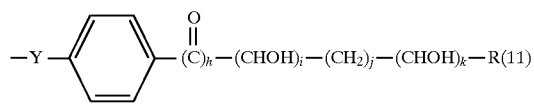

or

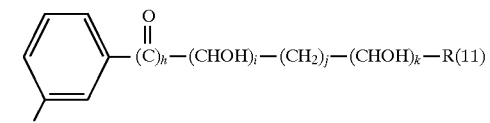

or

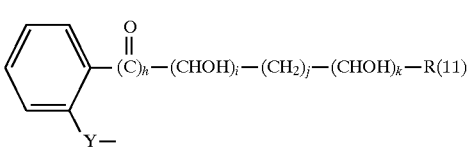

where Y=oxygen, S or —NR(12),
R(11) and R(12) independently are hydrogen or methyl,
h is zero or 1,
i and k independently of one another are zero, 1, 2 or 3,
j is zero or 1, but where h, i and k cannot simultaneously be zero,
R(3) is methyl, cyano, trifluoromethyl, F, Cl or hydrogen,
R(4) is hydrogen, OH or $NH_2$ and their pharmaceutically tolerable salts.

If one of the substituents R(1) to R(4) contains one or more centers of asymmetry, these can have either the S or R configuration. The compounds can be present as optical isomers, as diastereomers, as racemates or as mixtures thereof.

The designated alkyl radicals can be present either in straight-chain or branched form.

The invention furthermore relates to a process for the preparation of the compound I, which comprises reacting compounds of the formula II

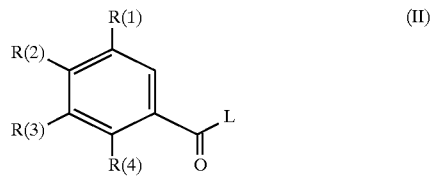

in which R(1) to R(4) have the given meaning and L is a leaving group which can be easily nucleophilically substituted, with guanidine.

The activated acid derivatives of the formula II in which L is an alkoxy group, preferably a methoxy group, a phenoxy group, a phenylthio, methylthio or 2-pyridylthio group, or a nitrogen heterocycle, preferably 1-imidazolyl, are advantageously obtained in a manner known per se from the carbonyl chlorides (formula II, L=Cl) on which they are based, which for their part can in turn be prepared in a manner known per se from the carboxylic acids (formula II, L=OH) on which they are based, for example using thionyl chloride.

In addition to the carbonyl chlorides of the formula II (L=Cl), other activated acid derivatives of the formula II can also be prepared in a manner known per se directly from the benzoic acid derivatives (formula II, L=OH) on which they are based, such as, for example, the methyl esters of the formula II where L=OCH₃ by treatment with gaseous HCl in methanol, the imidazolides of the formula II by treatment with carbonyldiimidazole [L=1-imidazolyl, Staab, Angew. Chem. Int. Ed. Engl. 1, 351–367 (1962)], the mixed anhydrides II using Cl—COOC₂H₅ or tosyl chloride in the presence of triethylamine in an inert solvent, and also the activation of benzoic acids using dicyclohexylcarbodiimide (DCC) or using O—[(cyano(ethoxycarbonyl)methylene) amino]-1,1,3,3-tetramethyluronium tetrafluoborate ("TOTU") [Proceedings of the 21. European Peptide Symposium, Peptides 1990, Editors E. Giralt and D. Andreu, Escom, Leiden, 1991]. A number of suitable methods for the preparation of activated carboxylic acid derivatives of the formula II are given under details of source literature in J. March, Advanced Organic Chemistry, Third Edition (John Wiley & Sons, 1985), p. 350.

The reaction of an activated carboxylic acid derivative of the formula I with guanidine is carried out in a manner known per se in a protic or aprotic polar but inert organic solvent. Methanol, isopropanol or THF from 20° C. to the boiling point of these solvents have proven suitable in the reaction of the methyl benzoates (II, L=OMe) with guanidine. In most reactions of compounds II with salt-free guanidine, the reaction was advantageously carried out in aprotic inert solvents such as THF, dimethoxyethane or dioxane. However, water can also be used as a solvent in the reaction of II and III if a base such as, for example, NaOH is used.

If L=Cl, the reaction is advantageously carried out with the addition of an acid scavenger, for example in the form of excess guanidine for binding the hydrohalic acid.

Some of the underlying benzoic acid derivatives of the formula II are known and described in the literature. The unknown compounds of the formula II can be prepared by methods known from the literature, by converting, for example, 4- (or 5-)halo-3-chlorosulfonylbenzoic acids into 3-aminosulfonyl-4-(or 5-)halobenzoic acids with ammonia or amines or into 3-alkylsulfonyl-4-(or 5-)halobenzoic acids with a weak reductant such as sodium bisulfite and subsequent alkylation, and reacting the resulting benzoic acids according to one of the process variants described above to give compounds I according to the invention.

The introduction of some substituents in the 4- and 5-position is carried out by methods known from the literature of palladium-mediated cross-coupling of aryl halides with, for example, organostannanes, organoboronic acids or organoboranes or organocopper or zinc compounds.

In general, benzoylguanidines I are weak bases and can bind acid with the formation of salts. Possible acid addition salts are salts of all pharmacologically tolerable acids, for example halides, in particular hydrochlorides, lactates, sulfates, citrates, tartrates, acetates, phosphates, methanesulfonates and p-toluenesulfonates.

The compounds I are substituted acylguanidines. The most prominent representative of the acylguanidines is the pyrazine derivative amiloride, which is used in therapy as a potassium-sparing diuretic. Numerous other compounds of the amiloride type are described in the literature, such as, for example, dimethylamiloride or ethylisopropylamiloride.

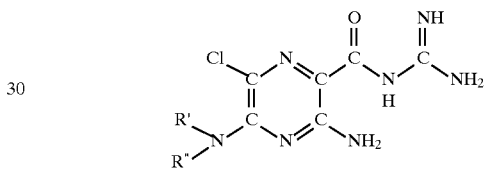

Amiloride: R', R"=H
Dimethylamiloride: R', R"=CH₃
Ethylisopropylamiloride: R'=C₂H₅, R"=CH(CH₃)₂

Investigations have moreover been disclosed which point to antiarrhythmic properties of amiloride [Circulation 79, 1257–63 (1989)]. Obstacles to wide use as an antiarrhythmic are, however, that this effect is only slightly pronounced and occurs accompanied by a hypotensive and saluretic action and these side effects are undesired in the treatment of cardiac arrhythmias.

Indications of antiarrhythmic properties of amiloride were also obtained in experiments on isolated animal hearts (Eur. Heart J. 9 (suppl.1): 167 (1988) (book of abstracts)). For instance, it was found in rat hearts that an artificially induced ventricular fibrillation could be suppressed completely by amiloride. The above mentioned amiloride derivative ethylisopropylamiloride was even more potent than amiloride in this model.

U.S. Pat. No. 5,091,394 (HOE 89/F 288) describes benzoylguanidines which carry a hydrogen atom in the position corresponding to the radical R(1). German Patent Application P 42 04 575.4 (HOE 92/F 034) proposes 3,5-substituted benzoylguanidines in which, however, the substituent R(2) does not have the meanings claimed according to the present invention.

In U.S. Pat. No. 3,780,027, acylguanidines are claimed which are structurally similar to the compounds of the formula I and are derived from commercially available loop diuretics, such as bumetanide. A strong salidiuretic activity is correspondingly reported for these compounds.

It was therefore surprising that the compounds according to the invention have no undesired and disadvantageous salidiuretic properties, but very good antiarrhythmic properties against arrhythmias of the type which occur, for example, in the case of oxygen deficiency symptoms.

As a result of their pharmacological properties, the compounds, as antiarrhythmic pharmaceuticals having a cardioprotective component, are outstandingly suitable for infarct prophylaxis and infarct treatment and for the treatment of angina pectoris, where they also preventively inhibit or greatly decrease the pathophysiological processes in the formation of ischemically induced damage, in particular in the production of ischemically induced cardiac arrhythmias. Because of their protective actions against pathological hypoxic and ischemic situations, the compounds of the formula I according to the invention can be used as a result of inhibition of the cellular $Na^+/H^+$ exchange mechanism as pharmaceuticals for the treatment of all acute or chronic damage caused by ischemia or primary or secondary diseases induced thereby. This relates to their use as pharmaceuticals for surgical interventions, for example in organ transplants, where the compounds can be used both for the protection of the organs in the donor before and during removal, for the protection of removed organs, for example during treatment with or storage thereof in physiological bath fluids, and during transfer to the body of the recipient. The compounds are also useful protective pharmaceuticals during the performance of angioplastic surgical interventions, for example in the heart and in peripheral vessels. In accordance with their protective action against ischemically induced damage, the compounds are also suitable as pharmaceuticals for the treatment of ischemias of the nervous system, in particular the CNS, where they are suitable, for example, for the treatment of stroke or of cerebral edema. Moreover the compounds of the formula I according to the invention are also suitable for the treatment of forms of shock, such as, for example, allergic, cardiogenic, hypovolemic and bacterial shock.

Moreover, the compounds of the formula I according to the invention are distinguished by potent inhibitory action on the proliferation of cells, for example fibroblast cell proliferation and the proliferation of vascular smooth muscle cells. The compounds of the formula I can therefore be considered as useful therapeutics for diseases in which cell proliferation is a primary or secondary cause, and can therefore be used as antiatherosclerotics, agents against diabetic late complications, cancers, fibrotic diseases such as pulmonary fibrosis, fibrosis of the liver or fibrosis of the kidneys, organ hypertrophies and hyperplasias, in particular in prostate hyperplasia or prostate hypertrophy.

The compounds according to the invention are active inhibitors of the cellular sodium-proton antiporter ($Na^+/H^+$ exchanger), which is also raised in numerous diseases (essential hypertension, atherosclerosis, diabetes, etc.) in those cells which are easily accessible to measurements, such as, for example, in erythrocytes, platelets or leucocytes. The compounds according to the invention are therefore suitable as excellent and simple scientific tools, for example in their use as diagnostics for the determination and differentiation of certain forms of hypertension, but also of atherosclerosis, diabetes, proliferative diseases etc. Moreover, the compounds of the formula I are suitable for preventive therapy for the prevention of the formation of high blood pressure, for example, essential hypertension.

Compared to the known compounds, the compounds according to the invention have a significantly improved water solubility. They are therefore significantly more highly suitable for i.V. administration.

Pharmaceuticals which contain a compound I can be administered orally, parenterally, intravenously, rectally or by inhalation, the preferred administration being dependent on the particular type of the disease. The compounds I can be used on their own or together with pharmaceutical auxiliaries, to be precise both in veterinary and in human medicine.

The auxiliaries which are suitable for the desired pharmaceutical formulation are familiar to the person skilled in the art on the basis of his expert knowledge. In addition to solvents, gelling agents, suppository bases, tabletting auxiliaries and other active compound excipients, antioxidants, dispersants, emulsifiers, antifoams, flavor correctants, preservatives, solubilizers or colorants, for example, can be used.

For a form for oral administration, the active compounds are mixed with the additives suitable for this purpose, such as excipients, stabilizers or inert diluents, and are brought by the customary methods into the suitable administration forms, such as tablets, coated tablets, hard gelatine capsules, or aqueous, alcoholic or oily solutions. Inert excipients which can be used are, for example, gum arabic, magnesia, magnesium carbonate, potassium phosphate, lactose, glucose or starch, in particular cornstarch. Preparation can be carried out here both as dry and as moist granules. Suitable oily excipients or solvents are, for example, vegetable or animal oils, such as sunflower oil or fish liver oil.

For subcutaneous or intravenous administration, the active compounds are brought into solution, suspension or emulsion, if desired using the substances customary for this purpose such as solubilizers, emulsifiers or other auxiliaries. Suitable solvents are, for example: water, physiological saline solution or alcohols, for example ethanol, propanol, glycerol, and also sugar solutions such as glucose or mannitol solutions, or alternatively a mixture of the various solvents mentioned.

Pharmaceutical formulations suitable for administration in the form of aerosols or sprays are, for example, solutions, suspensions or emulsions of the active compound of the formula I in a pharmaceutically acceptable solvent, such as, in particular, ethanol or water, or a mixture of these solvents.

If required, the formulation can also contain still other pharmaceutical auxiliaries such as surfactants, emulsifiers and stabilizers as well as a propellant gas. Such a preparation contains the active compound customarily in a concentration from about 0.1 to 10, in particular from about 0.3 to 3% by weight.

The dose of the active compound of the formula I to be administered and the frequency of administration depend on the potency and duration of action of the compounds used and additionally on the type and severity of the disease to be treated and on the sex, age, weight and individual responsiveness of the mammal to be treated. On average, the daily dose of a compound of the formula I in a patient of weight about 75 kg is at least 0.001 mg/kg, preferably 0.01 mg/kg, to at most 10 mg/kg, preferably 1 mg/kg of body weight. In acute episodes of the disease, for example immediately after suffering a cardiac infarct, even higher and in particular more frequent doses may be necessary, for example up to 4 individual doses per day. In particular when administered i.v., for example in the case of an infarct patient in the intensive care unit, up to 200 mg per day may be necessary.

List of abbreviations:

| | |
|---|---|
| MeOH | methanol |
| DMF | N,N-dimethylformamide |
| NBS | N-bromosuccinimide |

-continued

| | |
|---|---|
| AIBN | α,α-azobisisobutyronitrile |
| EI | electron impact |
| DCI | desorption-chemical ionization |
| RT | room temperature |
| EA | ethyl acetate (EtOAc) |
| DIP | diisopropyl ether |
| MTB | methyl tertiary butyl ether |
| mp | melting point |
| HEP | n-heptane |
| DME | dimethoxyethane |
| FAB | fast atom bombardment |
| $CH_2Cl_2$ | dichloromethane |
| THF | tetrahydrofuran |
| eq | equivalent |
| ES | electrospray ionization |

Experimental Section

General Procedure for the preparation of benzoylguanidines (I)

Variant A: from benzoic acids (II, L=OH)

0.01 mol of the benzoic acid derivative of the formula II is dissolved or suspended in 60 ml of anhydrous THF and then treated with 1.78 g (0.011 mol) of carbonyldiimidazole. After stirring for 2 hours at room temperature, 2.95 g (0.05 mol) of guanidine are introduced into the reaction solution. After stirring overnight, the THF is distilled off under reduced pressure (Rotavapor), the residue is treated with water, the mixture is adjusted to pH 6 to 7 with 2N HCL and the corresponding benzoylguanidine (formula I) is filtered off. The benzoylguanidines thus obtained can be converted into the corresponding salts by treatment with aqueous or methanolic or ethereal hydrochloric acid or other pharmacologically tolerable acids.

General procedure for the preparation of benzoylguanidines (I)

Variant B: from alkyl benzoates (II, L=O-alkyl)

5 mmol of the alkyl benzoate of the formula II and 25 mmol of guanidine (free base) are dissolved in 15 ml of isopropanol or suspended in 15 ml of THF and boiled under reflux (typical reaction time 2 to 5 h) until conversion is complete (thin-layer checking). The solvent is removed by distillation under reduced pressure (Rotavapor), the residue is taken up in 300 ml of EA and the solution is washed three times with 50 ml of $NaHCO_3$ solution each time. It is dried over $Na_2SO_4$, the solvent is removed by distillation in vacuo and the residue is chromatographed on silica gel using a suitable eluent, for example EA/MeOH 5:1. (For salt formation see Variant A).

EXAMPLE 1
4-(4-Acetylphenoxy)-3-methylsulfonylbenzoylguanidine

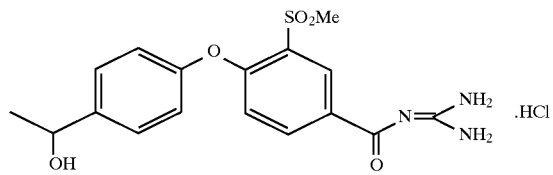

a) Methyl 4-(4-acetylphenoxy)-3-methylsulfonylbenzoate 5 mmol of methyl 4-chloro-3-methylsulfonylbenzoate, 15 mmol of $K_2CO_3$ and 5 mmol of 4-hydroxyacetophenone are stirred at 130° C. under argon in 10 ml of DMF (anhydrous) for 2 h. The DMF is then removed in vacuo, the residue is taken up using 50 ml of water and 50 ml of EA and the solution is extracted twice with 50 ml of EA. The extracts are dried over $Na_2SO_4$ and the solvent is removed in vacuo. Crystallization from diethyl ether yields 1.2 g of a light brown solid, m.p. 135° C.

$R_f$ (MTB)=0.41 MS (DCI): 349 (M+1)

b) 4-(4-Acetylphenoxy)-3-methylsulfonylbenzoylguanidine hydrochloride 1.2 mmol of ester 1a) and 6.0 mmol of guanidine are reacted according to general procedure B. 130 g of white powder, m.p.>270° C.

$R_f$ (EA/MeOH 5:1)=0.46 MS (DCI): 376 (M+1)

EXAMPLE 2
4-[4-(2(R,S)-Hydroxyethyl)phenoxy]methylsulfonylbenzoylguanidine hydrochloride

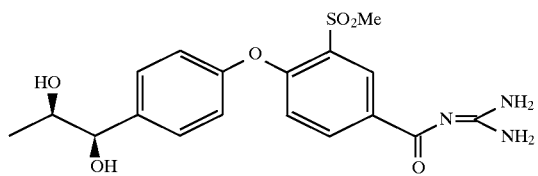

a) Ethyl 4-[4-(2(RS)-hydroxyethyl)phenoxyl]methylsulfonylbenzoate 2.4 mmol of ketone 1a) and 2.4 mmol of $NaBH_4$ are dissolved in 10 ml of ethanol (anhydrous) and the mixture is stirred at RT under argon for 20 h. 10 ml of water are then added, and the ethanol is removed in vacuo. 10 ml of saturated aqueous NaCl solution are then added, and the mixture is extracted 3 times with 20 ml of EA. The extracts are dried over $Na_2SO_4$ and the solvent is removed in vacuo. 700 mg of a pale yellow oil are obtained.

$R_f$ (MTB)=0.41 MS (DCI): 363 (M+1)

b) 4-[4-(2(R,S)-Hydroxyethyl)phenoxy]methylsulfonylbenzoylguanidine hydrochloride 1.9 mmol of ester 2a) and 9.6 mmol of guanidine are reacted according to the general procedure B. White powder, m.p.>270° C.

$R_f$ (EA/MeOH 10:1)=0.21 MS (DCI): 379 (M+1)

EXAMPLE 3
4-[4-(1(R),2(R) -Dihydroxyprop-1-yl)phenoxy]-3-methylsulfonylbenzoylguanidine

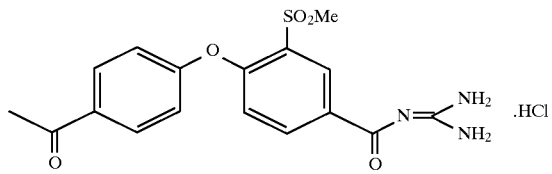

a) Methyl 4-(4-formylphenoxy)-3-methylsulfonylbenzoate 39 mmol of methyl 4-fluoro-3-methylsulfonylbenzoate, 39 mmol of 4-formylphenol and 78 mmol of $K_2CO_3$ are stirred at 130° C. under argon in 100 ml of DMF (anhydrous) for 3.5 h. The mixture is then poured into 300 ml of water and extracted 3 times with 300 ml of EA each time. The extracts are dried over $Na_2SO_4$ and the solvent is removed in vacuo. The residue is recrystallized from MTB, and 1.6 g of colorless solid are obtained.

$R_f$ (MTB)=0.59 MS (ES): 335 (M+1)

b) Methyl 4-(4-propen-1-ylphenoxy)-3-methylsulfonylbenzoate, E/Z mixture 7.2 mmol of ethyltriphenylphosphonium bromide are suspended in 50 ml of THF (anhydrous) and treated at RT with 6.7 mmol of potassium t-butoxide. The mixture is stirred at this temperature for 3 h and then cooled to 0° C., and a solution of 4.8 mmol of the aldehyde 3a) in 15 ml of THF is added dropwise. The mixture is stirred at RT for 1 h, then poured into 50 ml of saturated aqueous NaCl solution and extracted 3 times with 100 ml of EA. The extracts are dried over $Na_2SO_4$ and the solvent is removed in vacuo. Chromatography on silica gel using DIP yields 1.3 g of colorless oil.

$R_f$ (DIP)=0.40 MS (ES): 346 (M+1)

c) Methyl (E)-4-(4-propen-1-ylphenoxy)-3-methylsulfonylbenzoate 3.8 mmol of E/Z mixture 3b) and 3.8 mmol of iodine are allowed to stand at RT for 5 days in 50 ml of $CH_2Cl_2$. The mixture is poured into 50 ml of $Na_2SO_3$ solution and extracted twice with 50 ml of $CH_2Cl_2$. The extracts are dried over $Na_2SO_4$ and the solvent is removed in vacuo. 1.3 g of colorless oil.

d) Methyl 4-[4-(1(R), 2(R)-dihydroxyprop-1-yl)phenoxy]-3-methylsulfonylbenzoate 1.9 mmol of olefin 3c) and 2.6 g of AD mix a (J. Org. Chem. 1992, 57, p. 2769) are stirred at RT for 5 h in 9 ml of t-butanol and 9 ml of $H_2O$. 3 g of $Na_2SO_3$ are then added, and the mixture is stirred at RT for a further 30 min. It is then extracted 3 times with 50 ml of EA each time and dried over $Na_2SO_4$, and the solvent is removed in vacuo. Chromatography on silica gel using MTB yields 130 mg of colorless oil.

$R_f$ (MTB)=0.14 MS (ES, +LiCl): 387 (M+7)

e) 4-[4-(1(R),2(R)-Dihydroxyprop-1-yl)phenoxy]-3-methylsulfonylbenzoylguanidine 0.29 mmol of methyl ester 3d and 1.5 mmol of guanidine are reacted according to general procedure B. 29 mg, amorphous solid.

$R_f$ (EA/MeOH 5:1)=0.23 MS (ES): 408 (M+1)

The title compound of Example 4 is synthesized analogously to Example 3 using AD mix β.

EXAMPLE 4

4-[4-(1(S),2(S)-Dihydroxyprop-1-yl)phenoxy]-3-methylsulfonylbenzoylguanidine

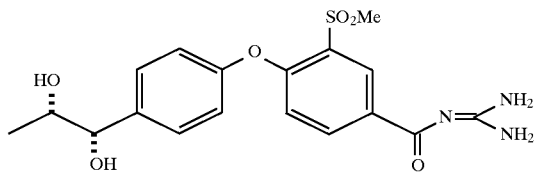

$R_f$ (EA/MeOH 5:1)=0.23 MS (ES): 408 (M+1)

Pharmacological data:

Inhibition of the $Na^+/H^+$ exchanger from rabbit erythrocytes

White New Zealand rabbits (Ivanovas) received a standard diet containing 2% cholesterol for six weeks in order to activate $Na^+/H^+$ exchange and thus to be able to determine the $Na^+$ influx into the erythrocytes via $Na^+/H^+$ exchange by flame photometry. The blood was taken from the auricular arteries and rendered uncoagulable by means of 25 IU of potassium heparin. A part of each sample was used for the duplicate determination of the hematocrit by centrifugation. Aliquots of 100 μl in each case were used to measure the $Na^+$ starting content of the erythrocytes.

In order to determine the amiloride-sensitive sodium influx, 100 μl of each blood sample were incubated at pH 7.4 and 37° C. in 5 ml in each case of a hyperosmolar salt-sucrose medium (mmol/l: 140 NaCl, 3 KCl, 150 sucrose, 0.1 ouabain, 20 trishydroxymethylaminomethane). The erythrocytes were then washed three times with ice-cold $MgCl_2$—ouabain solution (mmol/l: 112 mg $MgCl_2$, 0.1 ouabain) and hemolyzed in 2.0 ml of distilled water. The intracellular sodium content was determined by flame photometry.

The net $Na^+$ influx was calculated from the difference between sodium starting values and the sodium content of the erythrocytes after incubation. The amilorideinhibitable sodium influx ensued from the difference in the sodium content of the erythrocytes after incubation with and without amiloride $3 \times 10^{-4}$ mol/l. The sodium influx was also determined in this manner in the case of the compounds according to the invention.

Results

Inhibition of the $Na^+/H^+$ exchanger:

| Example | $IC_{50}$ μmol/l |
|---------|-----------|
| 1 | 0.4 |
| 2 | 0.4 |
| 3 | 0.3–0.5 |
| 4 | 0.1–0.5 |

We claim:

1. A benzoylguanidine of the formula I

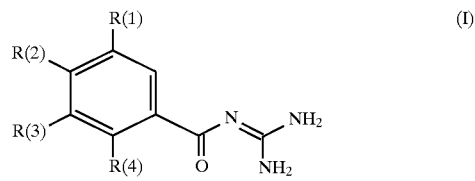

in which:

R(1) is hydrogen, F, Cl, Br, I, —$NO_2$, —C≡N,
$X_o$—$(CH_2)_p$—$(CF_2)_q$—$CF_3$, R(5)—$SO_m$, R(6)—CO— or R(6)R(7)N—$SO_2$—, where X is oxygen, S or NR(14), m is zero, 1 or 2, o is zero or 1, p is zero, 1 or 2, q is zero, 1, 2, 3, 4, 5 or 6, R(5) and R(6) are ($C_1$–$C_8$)-alkyl, ($C_3$–$C_6$)-alkenyl, —$C_nH_{2n}$—R(8) or $CF_3$, n is zero, 1, 2, 3 or 4, R(8) is ($C_3$–$C_7$)-cycloalkyl or phenyl which is unsubstituted or substituted by 1–3 substituents from the group comprising F, Cl, $CF_3$, methyl, methoxy and NR(9)R(10) where R(9) and R(10) are H or $C_1$–$C_4$-alkyl, where R(6) also has the meaning of H, R(7) is H or ($C_1$–$C_4$)-alkyl, R(2) is

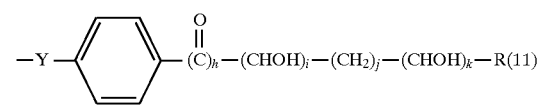

or

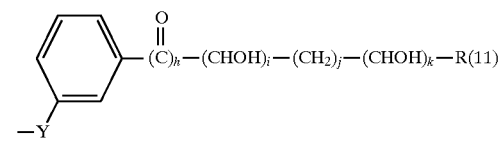

or

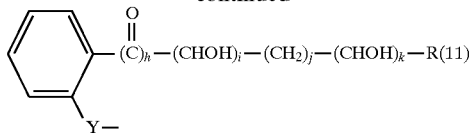

-continued where Y is oxygen, —S— or —NR(12)—,
R(11) and R(12)=hydrogen or ($C_1$–$C_3$)-alkyl, and
h is zero or 1, and
i, j and k independently are zero, 1, 2, 3 or 4, but where h, i and k are not simultaneously zero,
R(3) is defined as R(1), or is ($C_1$–$C_6$)-alkyl or —X—R(13) where
X is oxygen, S, NR(14),
R(14) is H or ($C_1$–$C_3$)-alkyl,
R(13) is H, ($C_1$–$C_6$)-alkyl, ($C_3$–$C_8$)-cycloalkyl or —$C_bH_{2b}$—R(15) where
b is zero, 1, 2, 3 or 4 and
R(15) is phenyl which is unsubstituted or substituted by 1–3 substituents from the group comprising F, Cl, $CF_3$, methyl, methoxy and NR(9)R(10) where R(9) and R(10) are H or ($C_1$–$C_4$)-alkyl,
R(4) is hydrogen, —OR(16) or —NR(16)R(17) where R(16) and R(17) are independently hydrogen or ($C_1$–$C_3$)-alkyl or its pharmaceutically tolerable salts.

2. A compound of the formula I as claimed in claim 1, in which:
R(1) is hydrogen, F, Cl, —C≡N, —$CF_3$, R(5)—$SO_m$, R(6)—CO— or R(6)R(7)N—$SO_2$—, where
m is zero, 1 or 2,
R(5) and R(6) are ($C_1$–$C_8$)-alkyl, ($C_3$–$C_4$)-alkenyl, —$C_nH_{2n}$—R(8) or —$CF_3$,
n is zero or 1,
R(8) is ($C_3$–$C_6$)-cycloalkyl or phenyl, which is unsubstituted or substituted by 1–3 substituents from the group comprising F, Cl, $CF_3$, methyl, methoxy and NR(9)R(10) where R(9) and R(10) are H or methyl,
where R(6) also has the meaning of H,
R(7) is H or methyl,
R(3) is hydrogen, methyl, cyano, —$CF_3$, F or Cl and the other radicals are as defined in claim 1, or its pharmaceutically tolerable salts.

3. A compound of the formula I as claimed in claim 1, in which:
R(1) is hydrogen, F, Cl, —C≡N, —$CF_3$, R(5)—$SO_m$, R(6)—CO— or R(6)R(7)N—$SO_2$—, where
m is zero, 1 or 2,
R(5) is methyl or $CF_3$,
R(6) and R(7) independently of one another are H or methyl;

R(2) is

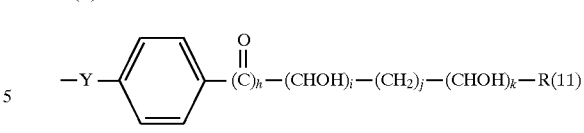

or

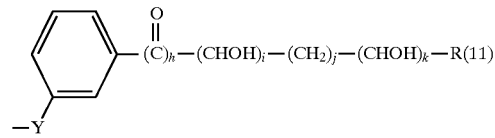

or

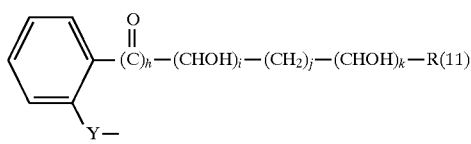

where Y=oxygen, S or —NR(12),
R(11) and R(12) independently are hydrogen or methyl,
h is zero or 1,
i and k independently of one another are zero, 1, 2 or 3,
j is zero or 1, but where h, i and k cannot simultaneously be is zero,
R(3) is methyl, cyano, trifluoromethyl, F, Cl or hydrogen,
R(4) is hydrogen, OH or $NH_2$ or its pharmaceutically tolerable salts.

4. A process for the preparation of a compound I as claimed in claim 1, which comprises reacting a compound of the formula II

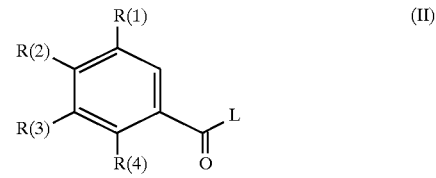

in which R(1) to R(4) have the given meaning and L is a leaving group which can be easily nucleophilically substituted, with guanidine.

5. A method for treating arrhythmias, which comprises administering to a host an effective amount of a compound of the Formula I as claimed in claim 1.

6. A medicament containing an effective amount of a compound I as claimed in claim 1.

* * * * *

UNITED STATES PATENT AND TRADEMARK OFFICE
CERTIFICATE OF CORRECTION

PATENT NO. : 5,880,156
DATED : March 9, 1999
INVENTOR(S) : Hans-Jochen Lang et al It is certified that error appears in the above-identified patent and that said Letters Patent is hereby corrected as shown below:

Title Page, Item [57], in the Abstract, delete lines 1-2 in their entirety, and in line 3, delete "pharmaceutical containing them".

Claim 3, Column 12, line 28, before "zero", delete "is".

Signed and Sealed this

Fifth Day of September, 2000

Attest:

Q. TODD DICKINSON

*Attesting Officer*  *Director of Patents and Trademarks*